(12) United States Patent
Gale

(10) Patent No.: US 7,323,191 B2
(45) Date of Patent: Jan. 29, 2008

(54) TRANSDERMAL WARFARIN SYSTEM

(75) Inventor: Robert M. Gale, Los Altos, CA (US)

(73) Assignee: Alza Corporation, Mountain View, CA (US)

( * ) Notice: Subject to any disclaimer, the term of this patent is extended or adjusted under 35 U.S.C. 154(b) by 597 days.

(21) Appl. No.: 10/900,804

(22) Filed: Jul. 27, 2004

(65) Prior Publication Data

US 2005/0025818 A1    Feb. 3, 2005

Related U.S. Application Data

(60) Provisional application No. 60/490,739, filed on Jul. 28, 2003.

(51) Int. Cl.
*A61F 13/00* (2006.01)
(52) U.S. Cl. .................................................. 424/449
(58) Field of Classification Search ............... 424/449, 424/94.4, 443, 444
See application file for complete search history.

(56) References Cited

U.S. PATENT DOCUMENTS

| | | | |
|---|---|---|---|
| 4,379,454 A | 4/1983 | Campbell et al. | |
| 5,120,546 A | 6/1992 | Hansen et al. | |
| 5,785,991 A | 7/1998 | Burkoth et al. | |
| 5,843,468 A | 12/1998 | Burkoth et al. | |
| 5,882,676 A | 3/1999 | Lee et al. | |
| 5,883,115 A | 3/1999 | Santus et al. | |
| 6,004,578 A | 12/1999 | Lee et al. | |
| 6,074,665 A | 6/2000 | Horstmann et al. | |
| 6,365,178 B1 | 4/2002 | Venkateshwaran et al. | |
| 6,379,696 B1 * | 4/2002 | Asmussen et al. | 424/449 |
| 6,512,010 B1 | 1/2003 | Gale et al. | |
| 2002/0009486 A1 | 1/2002 | Godbey | |
| 2002/0028235 A1 | 3/2002 | Reed et al. | |
| 2002/0110585 A1 | 8/2002 | Godbey et al. | |

FOREIGN PATENT DOCUMENTS

WO    WO 02/24159 A2    3/2002

OTHER PUBLICATIONS

International Search Report for corresponding PCT application No. PCT/US2004/024406.
Physician's Desk Reference—56th Edition, "Coumadin® Tablets", (2002); pp. 1243-1248.
Ridker, P.M. et al., "Long-Term, Low-Intensity Warfarin Therapy for the Prevention of Recurrent Venous Thromboembolism", The New England Journal of Medicine vol. 348, No. 15 (2003); pp. 1425-1434.
Satas, D., "Acrylic Adhesives", Handbook of Pressure-Sensitive Adhesive Technology, 2nd Edition (1989); pp. 396-456.

* cited by examiner

*Primary Examiner*—Sharon E. Kennedy

(57) ABSTRACT

Composition of matter for application to a body surface or membrane to administer warfarin by permeation through the body surface or membrane, the composition comprising warfarin to be administered, at a therapeutically effective rate, alone or in combination with a permeation enhancer or mixture. Also disclosed are drug delivery devices containing the warfarin or warfarin and enhancer composition and methods for the transdermal administration of the warfarin and warfarin/enhancer composition.

36 Claims, 4 Drawing Sheets

TRANSDERMAL WARFARIN SYSTEM

CROSS REFERENCE TO RELATED APPLICATIONS

This application claims the benefit of U.S. Provisional Application No. 60/490,739 filed Jul. 28, 2003.

TECHNICAL INVENTION

This invention relates to the safe and efficacious transdermal administration of warfarin for prophylaxis and treatment of thromboembolic disorders. More particularly, the invention relates to novel methods, compositions, and devices for administering warfarin to a subject through a body surface or membrane over an extended period of time.

BACKGROUND OF THE INVENTION

Warfarin, 3-((alpha)-acetonylbenzyl)-4-hydroxycoumarin, is an anticoagulant having demonstrated utility as a blood thinning and/or antithrombotic agent to prevent blood from clotting. Warfarin has been granted regulatory approval for the prophylaxis and/or treatment of venous thromboembolisms (VE) including deep vein thrombosis (DVT) and pulmonary embolism; prophylaxis and/or treatment of the thromboembolic complications associated with atrial fibrillation and/or cardiac valve replacement atrial fibrillation, to reduce the risk of death, recurrent myocardial infarction, and thromboembolic events such as stroke or systemic embolization after myocardial infarction. (See e.g., Physicians Desk Reference, 56$^{th}$ Edition, 2002, pages 1243-1248).

Warfarin is a potent anticoagulant having a relatively narrow therapeutic index (International Normalized Ratio (INR) of 2-4). Being potent means that relatively low concentrations of the drug in the blood are sufficient to produce the desired effect. Having a narrow therapeutic index means that the therapeutic effect is obtained only over a narrow range of concentrations; and in case of warfarin, concentrations below or above the range are associated with serious, and potential lethal side effects. The most serious risks associated with anticoagulant therapy with warfarin are hemorrhage in any tissue or organ and, necrosis and/or gangrene of skin and other tissues, possibly resulting in death or permanent disability.

Use of warfarin is further complicated by delay of a few days before the onset of the desired anticoagulant effect. Warfarin has a complex dose response relationship that makes safe and effective use a challenge. Treatment of each patient is a highly individualized matter. Once therapy is commenced, careful monitoring is necessary to strike a balance between underdosing and overdosing. For most indications, dosage is controlled by periodic determinations of prothrombin time (PT), International Normalized Ratio (INR) or other suitable coagulation tests. This combination of characteristics, coupled with the patient-to-patient variations in response to warfarin, dictates extreme caution in the administration of warfarin.

Until recently no therapeutic agent has been effective in long-term management of prophylaxis or treatment of recurrent venous thromboembolism due to high risk associated with anticoagulant therapy. A recent study (PREVENT) effectively demonstrated the use of low dose oral warfarin therapy for the long-term prevention of venous thromboembolism (VTE), including deep vein thrombosis (DVT) and pulmonary embolism, without significant adverse effects to the patients, such as major hemorrhage or other potential side effects of warfarin (See Ridker et al., *The New England Journal of Medicine* (*NEJM*), 348(15), pages 1425-1434).

Existing therapies consisting of oral administration of warfarin have several disadvantages. For example, frequent periodic doses result in peaks and valleys in blood concentration ($C_{peak}$~4 hr), and standard error are conventionally associated with those blood concentration swings. Further, lack of individual compliance and improper adherence to treatment schedule would result in warfarin concentrations below or above the prescribed dose causing serious, and potential lethal side effects. Thus there is a need for improved and effective prophylaxis and treatment of thromboembolic disorders.

The transdermal administration of warfarin offers several advantages. The peaks and valleys in blood concentration resulting from frequent periodic doses of warfarin would be eliminated and replaced by substantially constant plasma concentration. This would not only improve individual compliance but also would eliminate the alternating periods of high side-effects and ineffective blood concentrations associated with period dosing. Administering the agent through the skin directly into the blood stream would also eliminate first-pass metabolism of orally administered warfarin. However, transdermal administration of high doses of warfarin would result in unacceptable skin irritation and sensitization.

Previously described transdermal systems have been developed to administer warfarin in response to the aforementioned challenges. For example, U.S. Pat. No. 6,365,178 discloses transdermal systems containing hydrophilic salts of hydrophobic drugs dissolved in aqueous dispersion of hydrophobic pressure sensitive adhesives. Notwithstanding some success, previously described systems have not been entirely satisfactory for transdermal Transdermal administration of low-dose warfarin provides an effective regimen for long-term management of prophylaxis or treatment of recurrent venous thromboembolism due to high risk associated with anticoagulant therapy. A transdermal device capable of administering low-doses of warfarin would result in improved therapy by maintaining steady-state warfarin concentrations in the blood for periods of up to 7 days, preferably about 3 days to about 7 days.

SUMMARY OF THE INVENTION

The present invention provides safe and efficacious transdermal administration of low-dose warfarin for prophylaxis and treatment of thromboembolic disorders. In particular, the present invention provides novel methods, compositions, and devices for administering low-dose warfarin to a subject through a body surface or membrane over an extended period of time. In preferred embodiments, warfarin is present in a non-salt form, preferably, the non-ionized base form. The non-salt form of warfarin is preferred as it is expected to permeate human skin more readily than the ionized form. In particular, warfarin (preferably un-ionized warfarin) is dispersed/dissolved in a hydrophobic adhesive, wherein warfarin is highly soluble in the hydrophobic adhesive. The transdermal warfarin system of the invention is free of crystals, warfarin being present at or below saturation concentrations.

According to this invention, it has been discovered that warfarin can be safely and efficaciously administered transdermally at a low-dose to provide, an effective regimen for long-term prophylaxis and/or management of treatment of recurrent venous thromboembolism due to high associated with anticoagulant therapy, with a reduced incidence of side effects and improved individual compliance. Additionally improved compliance and substantially constant plasma concentration would result in less complications and reduce the frequency of monitoring, thus improving the cost-effectiveness of the therapy.

In addition, the present invention provides methods for the transdermal delivery of low-dose warfarin and delivery systems for effecting the same, which are suitable for the administration of low-dose warfarin continuously through a body surface or membrane to achieve and maintain therapeutic blood plasma levels of warfarin in an individual, preferably for long-term therapy. A particularly advantageous aspect of this invention is the ability to maintain substantially constant blood plasma levels of warfarin in an individual over extended periods of time.

BRIEF DESCRIPTION OF THE DRAWINGS

The foregoing and other objects, features and advantages of the present invention will be more readily understood upon reading the following detailed description in conjunction with the drawings in which.

DETAILED DESCRIPTION OF THE INVENTION

Overview and Definitions

Figure 1:
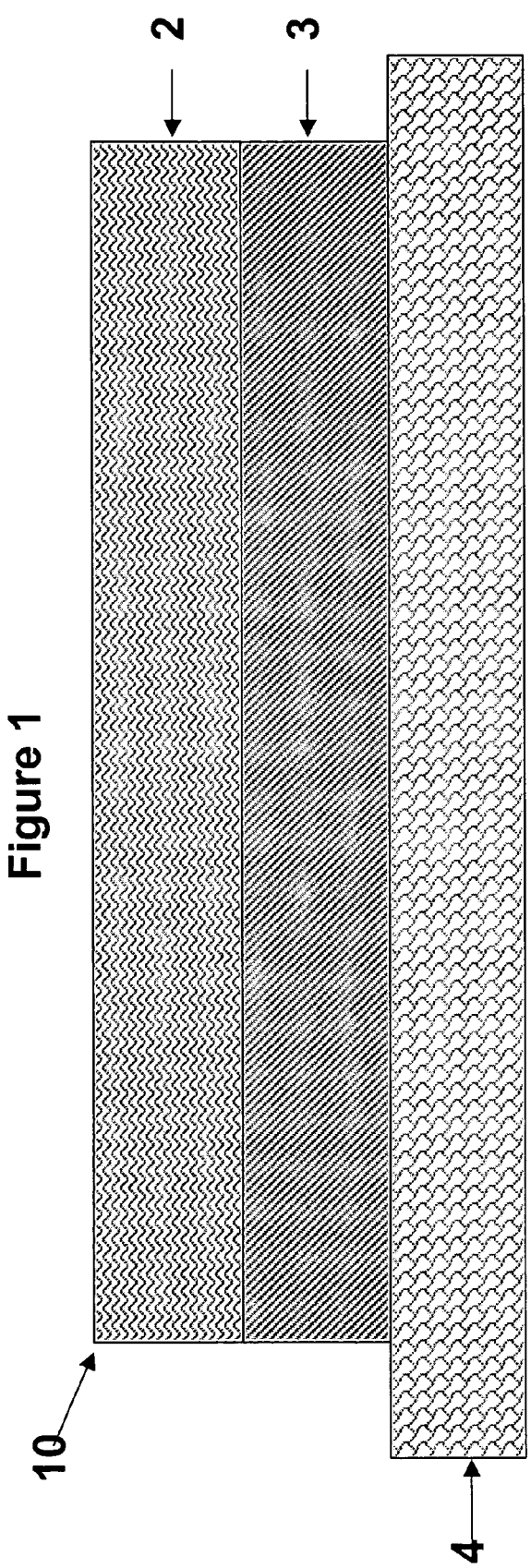
FIG. 1 illustrates a cross-section through a schematic, perspective view of one embodiment of transdermal therapeutic system according to this invention.

The present invention is directed to a safe and efficacious transdermal administration of low-dose warfarin for prophylaxis and treatment of thromboembolic disorders. In particular, the present invention provides novel methods, compositions, and devices for administering low-dose warfarin to a subject through a body surface or membrane over an extended period of time.

The practice of the present invention will employ, unless otherwise indicated, conventional methods used by those in pharmaceutical product development within those of skill of the art. Such techniques are explained fully in the literature. All patents, patent applications, and publications mentioned herein, whether supra or infra, are hereby incorporated by reference in their entirety.

In describing and claiming the present invention, the following terminology will be used in accordance with the definitions set out below.

The singular forms "a," "an" and "the" include plural referents unless the context clearly dictates otherwise. Thus, for example, reference to "a solvent" includes a single solvent as well as a mixture of two or more different solvents, reference to "a salt" includes a single salt as well as two or more different salts in combination, reference to "a polymer" includes a single polymer as well as a mixture of two or more different polymers, and the like.

As used herein, the term "transdermal" intends percutaneous and transmucosal administration, i.e., passage of warfarin through intact unbroken skin or mucosal tissue into the systemic circulation.

As used herein, the term "warfarin" intends not only the basic form of warfarin but also pharmaceutically acceptable salt forms of warfarin.

As used herein the term "salt" intends, but is not limited to, pharmaceutically acceptable salts such as sodium, potassium and the like.

As used herein, the term "warfarin therapy" intends all medical conditions for which warfarin is or will be indicated, including, without limitation, thromembolitic disorders arising from the obstruction or blocking of a blood vessel by a blood clot or thrombotic material dislodged from its site of origin, such as prophylaxis and/or treatment of venous thromboembolisms (VE) including deep vein thrombosis (DVT) and pulmonary embolism; prophylaxis and/or treatment of the thromboembolic complications associated with atrial fibrillation and/or cardiac valve replacement atrial fibrillation, to reduce the risk of death, recurrent myocardial infarction, and thromboembolic events such as stroke or systemic embolization after myocardial infarction.

As used herein, the term "low-dose warfarin therapy" intends administration of about 0.5 mg to about 2 mg of warfarin per day to achieve an INR of 1.25-2, preferably 1.5-2.

As used herein, the term "individual" intends a living mammal and includes, without limitation, humans and other primates, livestock and sports animals such as cattle, pigs and horses, and pets such as cats and dogs.

As used herein, the term "therapeutic blood plasma level" intends the level of warfarin in blood plasma that achieves a therapeutic effect and is typically within the range of about 1-2 $ng/mL\text{-}cm^2$; about 0.5-3 $ng/mL\text{-}cm^2$; and about 0.1-4 $ng/mL\text{-}cm^2$.

As used herein, the term "therapeutically effective rate" intends a rate of warfarin delivery effective to achieve therapeutic blood plasma levels of warfarin in an individual during the administration period, and to achieve an INR of 1.25-2, preferably 1.5-2.

As used herein, the phrase "sustained time period" or "administration period" intends at least about 8 hours and will typically intend a period in the range of about one to about seven days, preferably about 3 days to about 7 days of application.

As used herein, the phrase "predetermined area of skin" intends a defined area of intact unbroken skin or mucosal tissue. That area will usually be in the range of about 1 $cm^2$ to about 100 $cm^2$.

As used herein, the term "permeation enhancer" intends an agent or a mixture of agents that increases the permeability of the skin to warfarin.

As used herein, the term "permeation enhancement" intends an increase in the permeability of skin to warfarin in the presence of a permeation enhancer as compared to permeability of skin to warfarin in the absence of a permeation enhancer.

MODES OF CARRYING OUT THE INVENTION

As described previously, the present invention provides novel methods, compositions, and devices for administering low-dose warfarin to a subject through a body surface or membrane at a therapeutically effective rate for a predetermined, sustained time period in order to provide an effective therapeutic result. Another aspect of the present invention is directed to the transdermal administration of low-dose warfarin together with a suitable permeation enhancer or mixture of enhancers. Examples of suitable transdermal delivery devices are illustrated in FIGS. 1-4. In the figures, the same reference numbers are used throughout the different figures to designate the same or similar components. The figures are not drawn to scale.

Figure 2:
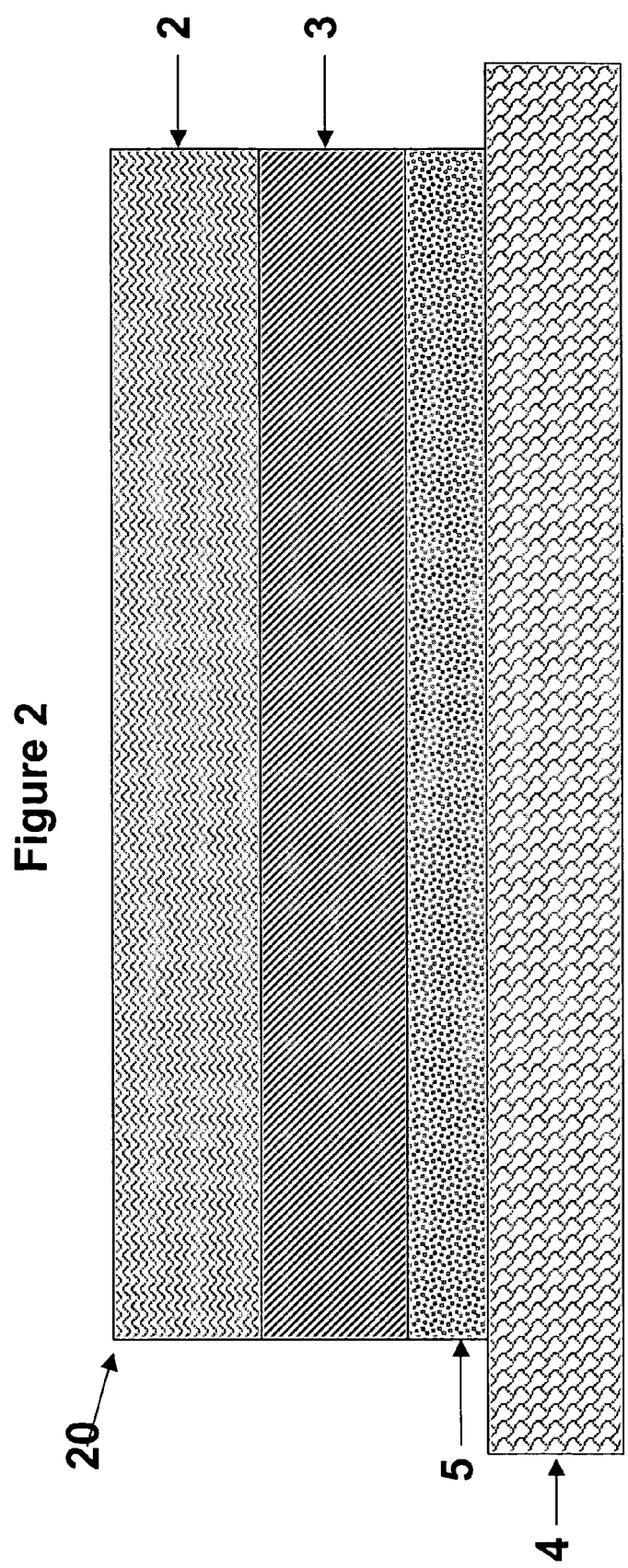
FIG. 2 illustrates a cross-section view through another embodiment of this invention.

Referring now to FIGS. 1 and 2, a preferred embodiment of the transdermal device 10 according to this invention comprises a backing layer 2, a warfarin reservoir 3 disposed on the backing layer 2, wherein at least the skin contacting surface of the warfarin reservoir 3 is adhesive, and a peelable protective layer 4. The warfarin reservoir 3 comprises warfarin, wherein warfarin is present at concentrations less than or equal to the saturation concentration, such that the warfarin reservoir 3 is free of warfarin crystals. In certain embodiments, the warfarin reservoir optionally comprises permeation enhancers, as described in greater detail below. In preferred embodiments, the warfarin reservoir 3 is formed from a pharmaceutically acceptable adhesive.

Referring now to FIG. 2, the warfarin reservoir 3 is formed from a material that does not have adequate adhesive properties. In this embodiment of a transdermal device 20, the skin contacting surface of the warfarin reservoir 3 may be formulated with a thin adhesive layer 5. A rate controlling membrane (not shown in FIGS. 1 and 2) for controlling the release rate of warfarin from the warfarin reservoir 3 to the skin may optionally be disposed on the skin contacting surface of the warfarin reservoir 3, wherein at least the skin contacting surface of the rate controlling membrane is adhesive.

Figure 3:
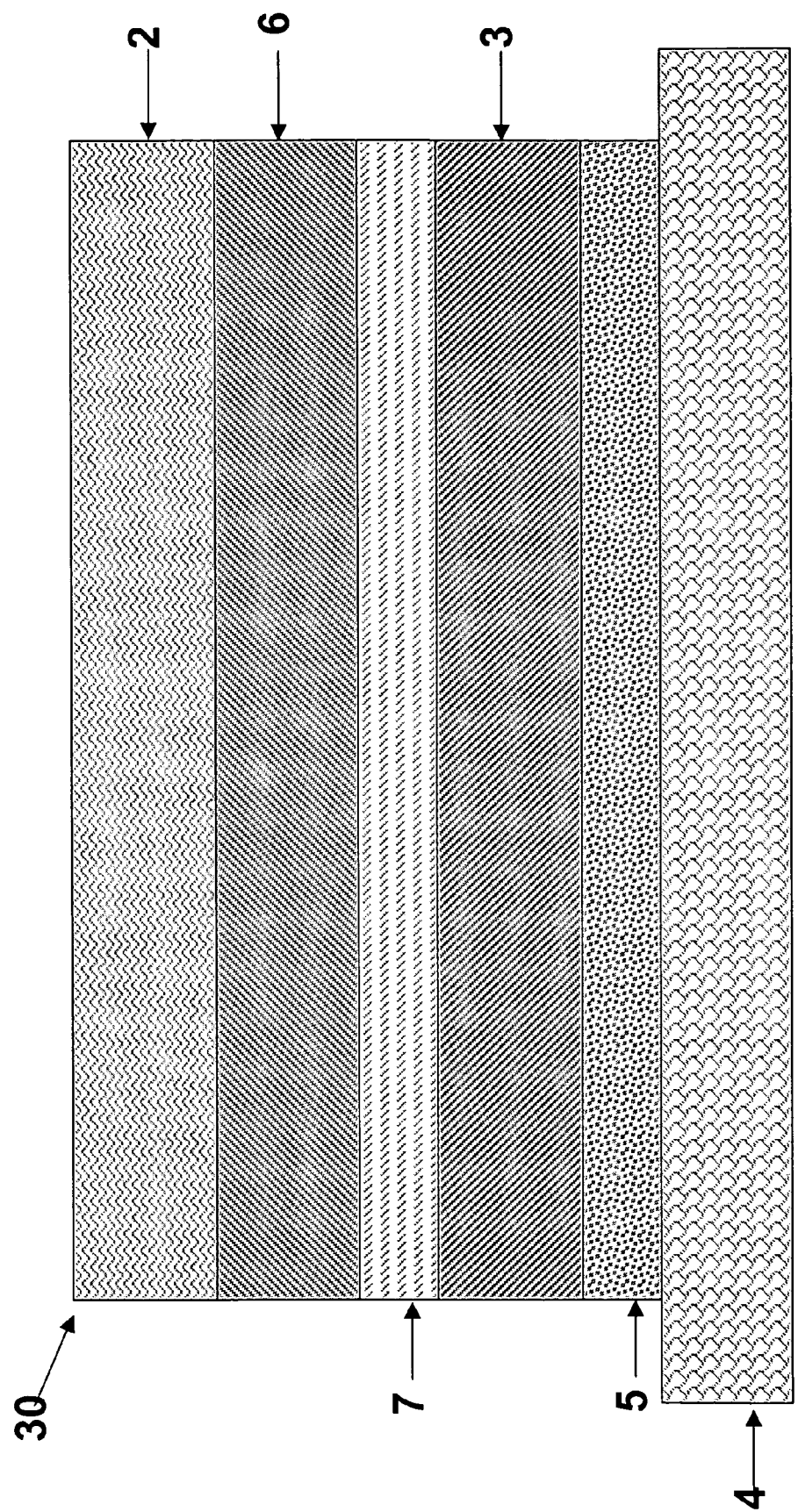
FIG. 3 illustrates a cross-section view through another embodiment of this invention.

In FIG. 3, transdermal delivery device 30 comprises a warfarin reservoir 3 substantially as described with respect to FIG. 1, the warfarin reservoir comprising warfarin and a permeation enhancer. The transdermal device further comprises a permeation enhancer reservoir ("enhancer reservoir") 6 having a permeation enhancer dispersed therethrough, wherein the permeation enhancer is at or below saturation and warfarin is at or above saturation. The enhancer reservoir 6 is preferably made from substantially the same material as is used to form warfarin reservoir 3. A rate-controlling membrane 7 for controlling the release rate of the permeation enhancer from enhancer reservoir 6 to warfarin reservoir 3 is placed between the two reservoirs. A rate-controlling membrane (not shown in FIG. 3) for controlling the release of warfarin and/or permeation enhancer from the device may also optionally be utilized and would be present between the adhesive layer 5 and the warfarin reservoir 3.

Superimposed over the permeation enhancer reservoir 6 of device 30 is a backing layer 2. On the skin-proximal side of warfarin reservoir 3 are an adhesive layer 5 and a peelable protective layer 4 which would be removed prior to application of the device 30 to the skin.

Figure 4:
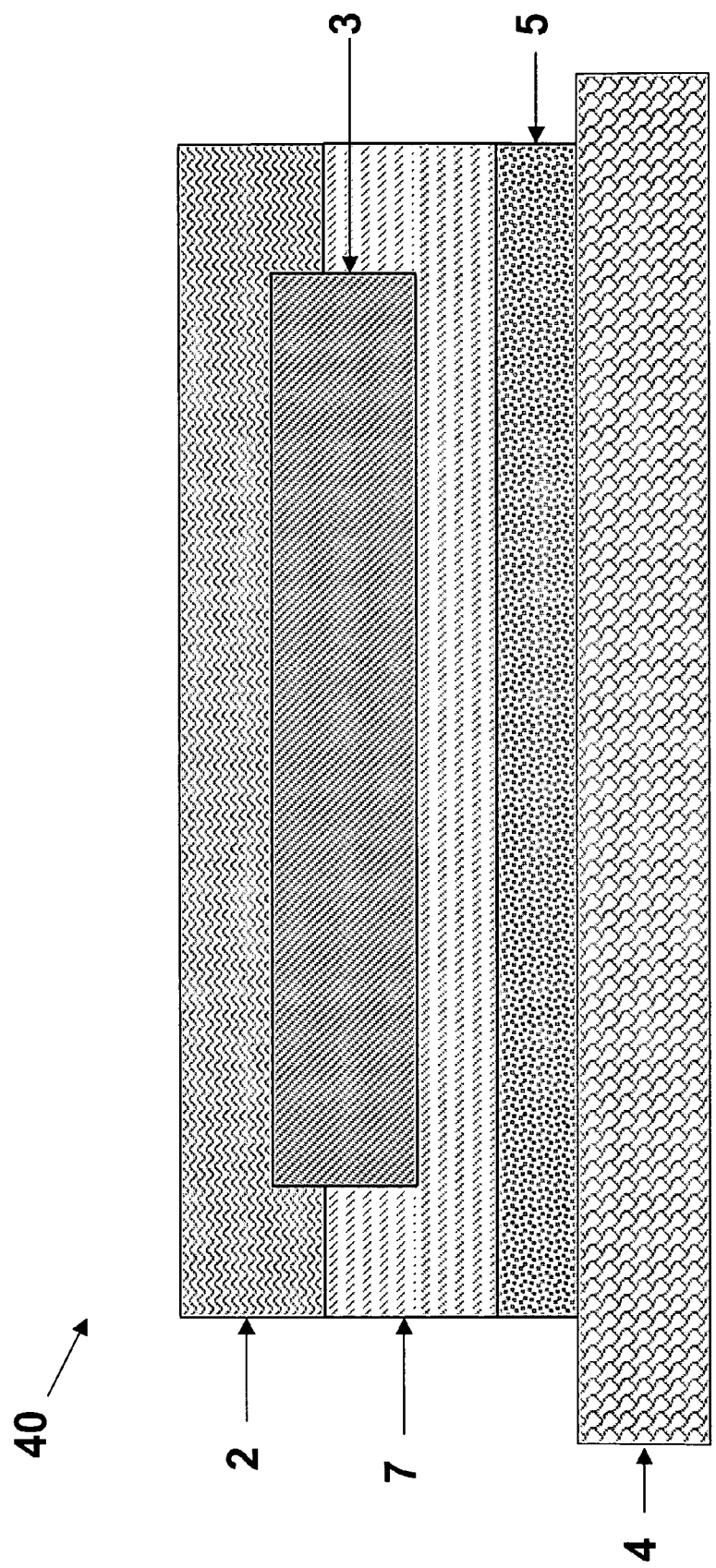
FIG. 4 illustrates a cross-section view through another embodiment of this invention.

In the embodiments of FIGS. 1, 2 and 3, the carrier or matrix material of the reservoirs has sufficient viscosity to maintain its shape without oozing or flowing. If, however, the matrix or carrier is a low-viscosity flowable material such as a liquid or a gel, the composition can be fully enclosed in a pouch or pocket, as known to the art from U.S. Pat. No. 4,379,454, for example, and as illustrated in FIG. 4. Device 40 shown in FIG. 4 comprises a backing layer 2 that serves as a protective cover for the device, imparts structural support, and substantially keeps components in device 40 from escaping the device. Device 40 also includes a warfarin reservoir 3, which contains warfarin with or without a permeation enhancer, and bears on its surface distant from backing member 2, a rate-controlling membrane 7 for controlling the release of warfarin and/or permeation enhancer from device 40. The outer edges of backing layer 2 overlay the edges of warfarin reservoir 3 and are joined along the perimeter with the outer edges of the rate-controlling membrane 7 in a fluid-tight arrangement. This sealed reservoir may be effected by pressure, fusion, adhesion, an adhesive applied to the edges, or other methods known in the art. In this manner, the warfarin reservoir 3 is contained wholly between the backing layer 2 and the rate-controlling membrane 7. On the skin-proximal side of rate-controlling membrane 7 are an adhesive layer 5 and a peelable protective layer 4 which would be removed prior to application of the device 40 to the skin.

In an alternative embodiment of device 40 of FIG. 4, the warfarin reservoir 3 contains a permeation enhancer and warfarin, wherein warfarin is at or below saturation. The warfarin and an additional amount of permeation enhancer are present in adhesive layer 5, which acts as a separate reservoir.

The backing layer 2 may be a breathable or occlusive material comprising fabric, polyvinyl acetate, polyvinylidene chloride, polyethylene, polyurethane, polyester, ethylene vinyl acetate (EVA), polyethylene terephthalate, polybutylene terephthalate, coated paper products, aluminum sheet and the like, and a combination thereof. In preferred embodiments, the backing layer comprises low density polyethylene (LDPE) materials, medium density polyethylene (MDPE) materials or high density polyethylene (HDPE) materials, e.g., SARANEX (Dow Chemical, Midland, Mich.). The backing layer may be a monolithic or a multilaminate layer. In preferred embodiments, the backing layer is a multilaminate layer comprising nonlinear LDPE layer/linear LDPE layer/nonlinear LDPE layer. The backing layer has a thickness of about 0.012 mm (0.5 mil) to about 0.125 mm (5 mil); preferably 0.025 mm (1 mil) to about 0.1 mm (4 mil); more preferably 0.0625 mm (1.5 mil) to about 0.0875 mm (3.5 mil).

The warfarin reservoir 3 is disposed on the backing layer, wherein at least the skin contacting surface of the reservoir is adhesive. The warfarin reservoir 3 may be formed from standard materials as known in the art. For example, the warfarin reservoir is formed from a polymeric material in which warfarin has reasonable solubility for warfarin to be delivered within the desired range, such as, a polyurethane, ethylene/vinyl acetate copolymer (EVA), polyacrylate, styrenic block copolymer, and the like. In preferred embodiments, the warfarin reservoir 3 is formed from a pharmaceutically acceptable pressure sensitive adhesive, preferably a polyacrylate or a styrenic block copolymer-based adhesive, as described in greater detail below.

The warfarin reservoir 3 or the adhesive layer 5 is formed from standard in-line contact adhesives and pressure sensitive adhesives known in the art. Examples of pressure sensitive adhesives include, but are not limited to, polyacrylates, polysiloxanes, polyisobutylene (PIB), polyisoprene, polybutadiene, styrenic block polymers, and the like. Examples of styrenic block copolymer-based adhesives include, but are not limited to, styrene-isoprene-styrene block copolymer (S IS), styrene-butadiene-styrene copolymer (SBS), styrene-ethylenebutene-styrene copolymers (SEBS), and di-block analogs thereof.

The present inventors also found that certain adhesives were preferred as the in-line contact adhesive when one was used in a therapeutic transdermal warfarin system. More particularly, it was found that systems using acrylate adhesives as the in-line contact adhesive resulted in greater flux of warfarin through skin than when other adhesives, such as polyisobutylene adhesives, were used.

The acrylic polymers are comprised of a copolymer or terpolymer comprising at least two or more exemplary components selected from the group comprising acrylic acids, alkyl acrylates, methacrylates, copolymerizable secondary monomers or monomers with functional groups.

Examples of monomers include, but are not limited to, acrylic acid, methacrylic acid, methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate, methoxyethyl methacrylate, and the like. Additional examples of appropriate acrylic adhesives suitable in the practice of the invention are described in Satas, "Acrylic Adhesives," Handbook of pressure-Sensitive Adhesive Technology, 2nd ed., pp. 396-456 (D. Satas, ed.), Van Nostrand Reinhold, N.Y. (1989). The acrylic adhesives are commercially available (National Starch and Chemical Corporation, Bridgewater, N.J.; Solutia, Mass.). Further examples of polyacrylate-based adhesives are as follows, identified as product numbers, manufactured by National Starch (Product Bulletin, 2000): 87-4098, 87-2287, 87-4287, 87-5216, 87-2051, 87-2052, 87-2054, 87-2196, 87-9259, 87-9261, 87-2979, 87-2510, 87-2353, 87-2100, 87-2852, 87-2074, 87-2258, 87-9085, 87-9301 and 87-5298.

The acrylic polymers comprise cross-linked and non-cross-linked polymers. The polymers are cross-linked by known methods to provide the desired polymers. In preferred embodiments, the adhesive is a polyacrylate adhesive having a glass transition temperature ($T_g$) less than −10° C., more preferably having a $T_g$ of about −20° C. to about −30° C. The molecular weight of the polyacrylate adhesive, expressed as weight average (MW), generally ranges from 25,000 to 10,000,000, preferably from 50,000 to about 3,000,000 and more preferably from 100,000 to 1,000,000 prior to any cross-linking reactions. Upon cross-linking the MW approaches infinity, as known to those involved in the art of polymer chemistry.

In preferred embodiments, the warfarin reservoir comprises about 1 wt % to about 30 wt % of warfarin; preferably about 2.5 wt % to about 28 wt % of warfarin; preferably about 4 wt % to about 26 wt % of warfarin; more preferably about 5 wt % to about 24 wt % of warfarin; more preferably about 6 wt % to about 22.5 wt % of warfarin; and even more preferably about 7 wt % to about 21 wt % of warfarin.

The material forming the warfarin reservoir 3 has a solubility for warfarin of about 0.1 wt % to about 22 wt % of the total polymer composition; preferably about 0.5 wt % to about 20 wt %; more preferably about 1.0 wt % to about 15 wt % of the total polymer composition; and even more preferably about 2 wt % to about 15 wt % of the total polymer composition. The warfarin reservoir 3, with or without the adhesive layer 5, has a thickness of about 0.025 mm to about 0.2 mm; preferably about 0.035 mm to about 0.15 mm; more preferably 0.045 mm to about 0.125 mm; and even more preferably about 0.05 mm to about 0.125 mm.

The enhancer reservoir 6 is formed from the same materials as described above for the formation of the warfarin reservoir. In preferred embodiments, the enhancer reservoir comprises about 5 wt % to about 25 wt % of permeation enhancer; preferably about 10 wt % to about 20 wt % of permeation enhancer. The enhancer reservoir 6 has a thickness of about 0.025 mm to about 0.2 mm; preferably about 0.035 mm to about 0.15 mm; more preferably 0.045 mm to about 0.125 mm; and even more preferably about 0.05 mm to about 0.125 mm.

The permeation enhancer useful in the present invention is selected from those compounds that are compatible with warfarin and which provide enhanced skin permeation to the drug when it is administered together with the drug to the skin of a user. Additionally, the permeation enhancer must not adversely interact with the adhesive of the in-line contact adhesive layer if one is present. An embodiment of this invention also relates to codelivery of at least one of the permeation enhancers mentioned above to aid in the transdermal delivery of warfarin.

Examples of permeation enhancers include, but are not limited to, fatty acid esters of glycerin, such as capric, caprylic, dodecyl, oleic acids; fatty acid esters of isosorbide, sucrose, polyethylene glycol; caproyl lactylic acid; laureth-2; laureth-2 acetate; laureth-2 benzoate; laureth-3 carboxylic acid; laureth-4; laureth-5 carboxylic acid; oleth-2; glyceryl pyroglutamate oleate; glyceryl oleate; N-lauroyl sarcosine; N-myristoyl sarcosine; N-octyl-2-pyrrolidone; lauraminopropionic acid; polypropylene glycol-4-laureth-2; polypropylene glycol-4-laureth-5dimethyl lauramide; lauramide diethanolamine (DEA), monoglycerides such as glycerol monolaurate (GML), glycerol monooleate (GMO) or glycerol monolinoleate, glyceryl monocaprylate, glyceryl monocaprate, lactate esters such as lauryl lactate, methyl laurate, caproyl lactic acid, lauramide diethanolamine (LDEA), dimethyl lauramide, polyethylene glycol-4 lauryl ether (Laureth-4), lauryl pyroglutamate (LP), sorbitan monolaurate and ethanol, alone or in combinations of one or more. Additional examples of suitable permeation enhancers are described, for example, in U.S. Pat. Nos. 5,785,991; 5,843,468; 5,882,676; and 6,004,578.

Typically, monoglycerides have been available as a mixture of monoglycerides of fatty acids with one monoglyceride being the principal component, from which component the mixture derives its name. For example, one commercial monoglyceride is Emerest 2421 glycerol monooleate (Emery Division, Quantum Chemical Corp.), which is a mixture of glycerol oleates with a glycerol monooleate content of 58% and a total monoesters content of 58%. Other examples of commercial monoglycerides are Myverol 1899K glycerol monooleate (Eastman Chemical Products) which has a glycerol monooleate content of 61% and a total monoesters content of 93%, and Myverol 1892K glycerol monolinoleate which has a glycerol monolinoleate content of 68% and a minimum total monoesters content of 90%. The monoesters are chosen from those with from 10 to 20 carbon atoms. The fatty acids may be saturated or unsaturated and include, for example, lauric acid, myristic acid, stearic acid, oleic acid, linoleic acid and palmitic acid. Monoglyceride permeation enhancers include glycerol monooleate, glycerol monolaurate and glycerol monolinoleate, for example. In a presently preferred embodiment of this invention, the permeation enhancer comprises glycerol monolaurate as the monoglyceride.

It has been seen that glycerol monooleate having a total monoesters content of less than about 65% interacts adversely with known adhesive materials to such an extent that the adhesive cannot function to maintain a delivery device on the skin. Therefore, when an in-line adhesive is present as a part of the device of the invention so that a permeation enhancer must pass through the adhesive, and when glycerol monooleate is utilized as the permeation enhancer, the glycerol monooleate must have a total monoesters content of at least 65%.

The permeation-enhancing mixture is dispersed through the matrix or carrier, preferably at a concentration sufficient to provide permeation-enhancing amounts of enhancer in the reservoir throughout the anticipated administration period. Where there is an additional, separate permeation enhancer matrix layer as well, the permeation enhancer normally is present in the separate reservoir in excess of saturation.

In additional embodiments, the warfarin reservoir 3 and/or the enhancer reservoir 6 may optionally contain additional components such as, additives, permeation enhancers, stabilizers, dyes, pigments, diluents, plasticizer, tackifying agent, pigments, carriers, inert fillers, antioxidants, excipients, gelling agents, anti-irritants, vasoconstrictors and other materials as are generally known to the transdermal art.

In certain embodiments, the warfarin reservoir 3 and/or the enhancer reservoir 6 comprises diluent materials capable of reducing quick tack, increasing viscosity, and/or toughening the matrix structure, such as polybutylmethacrylate (ELVACITE, manufactured by ICI Acrylics, e.g., ELVACITE 1010, ELVACITE 1020, ELVACITE 20), high molecular weight acrylates, i.e., acrylates having an average molecular weight of at least 500,000, and the like.

In certain embodiments, a plasticizer or tackifying agent is incorporated in the adhesive composition to improve the adhesive characteristics. Examples of suitable tackifying agents include, but are not limited to, aliphatic hydrocarbons; aromatic hydrocarbons; hydrogenated esters; polyterpenes; hydrogenated wood resins; tackifying resins such as ESCOREZ, aliphatic hydrocarbon resins made from cationic polymerization of petrochemical feedstocks or the thermal polymerization and subsequent hydrogenation of petrochemical feedstocks, rosin ester tackifiers, and the like; mineral oil and combinations thereof.

The tackifying agent employed should be compatible with the blend of polymers. For example, the styrenic block copolymers can be formulated with rubber compatible tackifying resins, end-block compatible resins such polymethyl styrene, or plasticizers such as mineral oil. Generally the polymer is about 5-50% of the total adhesive composition, the tackifier is about 30-85% of the total adhesive composition, and the mineral oil is about 2-40% of total adhesive composition.

The transdermal device as described in FIGS. 1-4 further comprises a peelable protective layer 4. The protective layer 4 is made of a polymeric material that may be optionally metallized. Examples of the polymeric materials include polyurethane, polyvinyl acetate, polyvinylidene chloride, polypropylene, polycarbonate, polystyrene, polyethylene, polyethylene terephthalate, polybutylene terephthalate, paper, and the like, and a combination thereof. In preferred embodiments, the protective layer comprises a siliconized polyester sheet.

In certain embodiments, the transdermal device as described in FIGS. 1-4 comprises a rate-controlling membrane. The rate-controlling membrane may be fabricated from permeable, semipermeable or microporous materials which are known in the art to control the rate of agents into and out of delivery devices and having a permeability to the permeation enhancer lower than that of warfarin reservoir 3. Suitable materials include, but are not limited to, polyethylene, polyvinyl acetate, ethylene n-butyl acetate and ethylene vinyl acetate copolymers.

A wide variety of materials which can be used for fabricating the various layers of the transdermal delivery patches according to this invention have been described above. This invention therefore contemplates the use of materials other than those specifically disclosed herein, including those which may hereafter become known to the art to be capable of performing the necessary functions.

Administration of Warfarin

Warfarin with or without the permeation enhancer can be administered to human skin or mucosa by direct application to the skin or mucosa in the form of an ointment, gel, cream or lotion, for example, but are preferably administered from a skin patch or other known transdermal delivery device which contains a saturated or unsaturated formulation of the warfarin or warfarin and enhancer.

The amount of warfarin present in the therapeutic device and required to achieve an effective therapeutic result depends on many factors, such as the minimum necessary dosage of the warfarin for the particular indication being treated; the solubility and permeability of the matrix, taking into account the presence of a permeation enhancer, of the adhesive layer and of the rate-controlling membrane, if present; and the period of time for which the device will be fixed to the skin. The minimum amount of warfarin is determined by the requirement that sufficient quantities of warfarin must be present in the device to maintain the desired rate of release over the given period of application. The maximum amount for safety purposes is determined by the requirement that the quantity of warfarin present cannot exceed a rate of release that reaches toxic levels.

Preferably, warfarin is present in the reservoir at a level below saturation for continuous administration to the skin or mucosal site at a therapeutic rate and for a period of time sufficient to deliver a therapeutically effective amount of warfarin that provides the desired therapeutic result. Alternatively, warfarin can be present in the matrix or carrier at a concentration in excess of saturation, the amount of excess being a function of the desired length of the delivery period of the system.

On application to the skin, warfarin in the warfarin reservoir 3 of the transdermal device as described in FIGS. 1-4 diffuses into the skin where it is absorbed into the bloodstream to produce a systemic anticoagulant effect. On repeated sequential application, the residual warfarin in the application site of the patch is absorbed by the body at approximately the same rate as warfarin from the new patch is absorbed into the new application area. Thus the patient should not experience any interruption of anticoagulant activity.

When long term low-dose warfarin therapy is desired the depleted patch would be removed and a fresh patch is applied to a new location. For example, the patch would be sequentially removed and replaced with a fresh patch at the end of the administration period to provide long term low-dose warfarin therapy. Since absorption of warfarin from the fresh patch into the new application area usually occurs at substantially the same rate as absorption by the body of the residual warfarin within the previous application site of the patch, blood levels will remain substantially constant.

Administration is maintained for at least three days, and up to 7 days, with 3-4 day regimen being considered preferable. In preferred embodiments, at least 3%, but not more than 40%, of the total amount of warfarin in the patch is administered during approximately the first 24 hours of use; at least 6%, but not more than 50%, of the total amount of warfarin is administered during approximately the first 48 hours of use; and at least 10%, but not more than 75%, of the total amount of warfarin is administered during the administration period.

Therapeutic blood plasma levels of about 1-2 ng/mL-cm$^2$; about 0.5-3 ng/mL-cm$^2$; and about 0.1-4 ng/mL-cm2 are achieved according to this invention. The desired rate for low-dose warfarin administration may be achieved by increasing or decreasing the surface area of the transdermal delivery device without affecting the flux. For example, for a warfarin skin flux of 6 μg/h-cm$^2$, a patch having a surface area of about 20 cm$^2$ would deliver approximately 2.4 mg of warfarin over a 24 hour period.

Because of the wide variation in skin permeability from individual to individual and from site to site on the same body, it may be preferable that the warfarin, with or without a permeation enhancer, be administered from a rate controlled transdermal delivery device. Rate control can be obtained either through a rate controlling membrane or adhesive or both as well as through the other means.

A certain amount of warfarin will bind reversibly to the skin, and it is accordingly preferred that the skin-contacting layer of the device include this amount of warfarin as a loading dose.

The surface area of the device of this invention can vary from about 1-200 cm$^2$. A typical device, however, will have a surface area within the range of about 1-50 cm$^2$, preferably about 20 cm$^2$.

The devices of this invention can be designed to effectively deliver warfarin for an extended time period of from several hours up to 7 days or longer.

Seven days is generally the maximum time limit for application of a single device because the adverse effect of occlusion of a skin site increases with time and the normal cycle of sloughing and replacement of the skin cells occurs in about 7 days.

Preferably, the transdermal drug delivery device contains sufficient amounts of a permeation enhancer as described above and warfarin, in combination, to provide systemic administration of warfarin through the skin at a therapeutically effective rate during the administration period in order to provide therapeutic blood plasma levels.

The aforementioned patents describe a wide variety of materials which can be used for fabricating various layers or components of the transdermal warfarin delivery systems according to this invention. This invention, therefore, contemplates the use of other materials other than those specifically disclosed herein including those that may become hereafter known to the artist capable of forming the necessary functions.

The invention is also directed to a method of continuously administering warfarin to an individual at a therapeutically effective rate during an administration period in order to provide substantially constant therapeutic blood plasma levels of warfarin in an individual.

Another method of the present invention is directed to a method for the transdermal coadministration of warfarin at a therapeutically effective rate together with a skin permeation-enhancing amount of a permeation enhancer in order to achieve and maintain therapeutic blood plasma levels of warfarin in an individual, comprising: coadministering to a body surface or membrane, warfarin; and a permeation enhancer, wherein warfarin is delivered at a therapeutically effective rate during the administration period in order to achieve and maintain therapeutic blood plasma levels of warfarin in an individual. The warfarin and permeation enhancer may be administered to the body surface or membrane by means of the devices and compositions described above.

A preferred embodiment of the present invention comprises a method of treating thromembolic disorders as described in detail above. The precise therapeutic dosage of warfarin will vary with the age, size, sex and condition of the subject, the nature and severity of the disorder to be treated, and the like; thus, a precise effective amount cannot be specified in advance and will be determined by the caregiver. However, appropriate amounts may be determined by routine experimentation to achieve an INR of 1.25-2, preferably 1.5-2.

The length of time of warfarin presence and the total amount of warfarin in the plasma can be changed following the teachings of this invention to provide different treatment regimens. Thus, they can be controlled by the amount of time during which exogenous warfarin is delivered transdermally to an individual or animal.

Methods of Manufacture

The transdermal devices are manufactured according to known methodology. A solution of the polymeric reservoir material, as described above, is added to a double planetary mixer, followed by addition of desired amounts of the warfarin, preferably 15 W % solids, and optionally, a permeation enhancer. Preferably, the polymeric reservoir material is an adhesive polymer, which is solubilized in an organic solvent, e.g., ethanol, ethyl acetate, hexane, and the like. The mixer is then closed and activated for a period of time to achieve acceptable uniformity of the ingredients. The mixer is attached by means of connectors to a suitable casting die located at one end of a casting/film drying line. The mixer is pressurized using nitrogen to feed solution to the casting die. Solution is cast as a wet film onto a moving siliconized polyester web. The web is drawn through the lines and a series of ovens are used to evaporate the casting solvent to acceptable residual limits. The dried reservoir film is then laminated to a selected backing membrane and the laminate is wound onto the take-up rolls. In subsequent operations, individual transdermal patches are die-cut, separated and unit-packaged using suitable pouchstock. The transdermal devices are cartoned using conventional equipment. In another process, the warfarin reservoir can be formed using dry-blending and thermal film-forming using equipment known in the art. Preferably, the materials are dry blended and extruded using a slot die followed by calendering to an appropriate thickness.

EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Specific examples of various transdermal patches of the invention which are capable of administering warfarin for extended periods of time will be described in the examples set for hereinafter. In the following examples all percentages are by weight unless noted otherwise.

Example 1

Ethylene-vinyl acetate co-polymer (1 Kg, 40 W % vinyl acetate) is weighed into the hopper of a Ross internal mixing bowl (Model PVM-2 or PD-2, Charles Ross & Sons Co., Hauppauge, N.Y.). The bowl is connected to the drive unit of a Brabender Mixing Bowl (Model R.E.O.-6) (C.W. Brabender Instruments, Inc., South Hackensack, N.J.). The top of the bowl is closed and the mixer is operated without heat, until an even melt is obtainer from the added pellets (about 0.5 h). At the end of this time the unit is stopped and the lid is opened. Warfarin acetate (150 gm) is added to the bowl. After the lid is closed, the unit is energized to achieve an even dispersion of warfarin in the co-polymer (0.5 h). The mixture is removed from the mixer and stored for further use.

A Brabender extrusion machine (0.75 inch diameter, 4 feet, single screw machine, Model 2503) (C.W. Brabender Instruments, Inc., South Hackensack, N.J.), is attached to a similar preparatory drive machine as described above. A heatable four-inch width flex-nip extrusion die is affixed to the end of the extrusion barrel. The extrudate is sandwiched between one interleaving siliconized polyester film and one polyester/EVA backing film. A set of three calender rolls is set up to size the warfarin-containing layer measuring six inch wide as it exits from the extruder. The target warfarin reservoir film thickness of 0.1+/−0.01 mm is achieved by appropriate adjustment of the calender rolls. The trilaminate is wound on a take-up roll for further manufacturing use.

A solution acrylate adhesive (product number 87-4287, National Starch and Chemical Corporation, Bridgewater, N.J.; Solutia, Mass.) in ethyl acetate is cast using a casting machine to form an adhesive layer. The solution is pressure-fed from a reservoir pot, through a slot die onto a relatively easy release siliconized polyester film. The film/adhesive bilayer is drawn through the heated stages of a dynamic oven to remove the ethyl acetate to less than 500 µg/gm levels. As the film exits the last stage of the drying ovens, the peelable layer is removed from the warfarin reservoir film and the adhesive layer is laminated to the available surface of the laminate. The four-layer film (PET/EVA layer, warfarin reservoir, acrylate adhesive & peelable liner) is wound on take-up rolls for further processing.

Individual transdermal systems are die-cut to 20 cm² area. In a final manufacturing step, systems are slit and packaged in Surlyn/Al/Kraft laminate pouchstock (Alcoa Flexiable Packaging, Richmond, Va.), with a terminal heat-sealing step. The device is capable of delivering warfarin at 2-15 µg/h-cm² for up to 7 days, preferably for about 3-7 days.

Example 2

The example illustrates the use of a continuous feeder-extruder (such as a Kneader extruder (Model MKS 30) Coperion Corp., Ramsey N.J.). A solid adhesive (such as a melt-processible acrylate, for example SEBS (stryene-ethylene/butylene-stryene) polymers Kraton SEBS G1657, from Kraton Polymers, Houston, Tex.) is continuously fed to a hopper, while warfarin base is fed into a second hopper on the extruder. The ratio of adhesive to polymer is 4:1. The extruded film is calendered downstream from the extrusion die between a siliconized polyester (3 mil) and a backing film comprised of polyester/polyethylene (2 mil), to a thickness of 0.125, +/−0.0125 mm, at a width of approximately 6.5 inches. The systems are die-cut to an area ranging from about 5 cm² to about 50 cm². The in vitro transdermal warfarin base for a 30 cm² system is nominally 7 µg/h-cm², when it is measured using standard two-sided skin flux cells. The duration of such systems is about 3 days to about 7 days.

If a greater transdermal warfarin flux is desired, the warfarin reservoir is formulated to contain as much as 15 W % permeation enhancer (for example lauryl proline ester, glycerol monolaurylate or oleic acid). Use of permeation enhancers would increase the flux 2-3 times over comparable devices with permeation enhancers.

Example 3

To improve the warfarin blood level variation, a rate control membrane can be manufactured and interposed between the warfarin reservoir and the acrylate layer to regulate the warfarin release. Depending upon the rate desired, an EVA film of 6-18.8% vinyl acetate, at a thickness of about 0.05 mm could be inserted.

Example 4

The warfarin/permeation enhancer reservoirs are prepared by mixing ethylene vinyl acetate having a vinyl acetate content of 40 percent ("EVA 40", USI Chemicals, Illinois), with warfarin base, GML (Grindsted Products, Braband, Denmark) or LDEA (Lonza, Inc.), and mineral oil (Witco Corp.). The mixture is then dissolved in tetrahydrofuran. After blending, the mixture is hand cast and dried to a 0.12 mm thick film.

The film is then laminated to a pigmented medium density polyethylene/aluminum foil/PET/EVA (Medpar®) backing on one side and an acrylate contact adhesive on the opposite side (3M, St. Paul, Minn.). The laminate is punched down to an area of 1.6 cm².

Circular pieces of human epidermis are placed with stratum corneum facing up. The release liner of the laminate is removed and the system is centered over the stratum corneum side of the epidermis. The edges of epidermis are then folded around the system. This assembly is mounted on a Teflon rod. A known volume of receptor solution is placed in a test tube and is equilibrated at 35° C. The Teflon rod with system and epidermis attached is then placed in a water bath at 35° C. Mixing is accomplished by attachment to a motor that causes constant vertical mixing.

At given time intervals, the entire receptor solution is removed from the test tubes and replaced with an equal volume of fresh receptor solutions previously equilibrated at 35° C. The receptor solutions are stored in capped vials at room temperature until assayed for warfarin content by HPLC. From the warfarin concentration and the volume of the receptor solutions, the area of permeation and the time interval, the flux of the warfarin through the epidermis is calculated as follows: (warfarin concentration×volume of receptor)/(area×time)=flux (1 g/cm²-hr).

Example 5

The warfarin/permeation enhancer reservoirs are prepared according to Example 4. The film is laminated to Medpar backing on one side and a polyisobutylene adhesive containing 2.5% by weight of warfarin on the other. The adhesive is prepared by dissolving 19.8% 1.2M polyisobutylene, 24.7% 35K polyisobutylene and 55.5% light mineral oil in heptane. The 2.5% warfarin is added and the entire mixture is cast to a dry thickness of 0.5 mm. The film is cut into circles using a stainless steel punch with an area of 1.6 cm².

The epidermis is separated from the dermis of the skin donor after immersion in 60° C. water for 60 seconds. Discs (⅞-inch diameter) are cut from the epidermis, and the discs are kept at 4° C. in a hydrated state until they are used.

For each device tested, the release liner is removed and the warfarin-releasing surface is placed against the stratum corneum side of a disc of epidermis that is blotted dry just prior to use. The excess epidermis is wrapped around the device so that none of the device edge is exposed to the receptor solution. The device covered with epidermis is attached to the flat side of the Teflon holder of a release rate rod using nylon netting and nickel wire. The rods are reciprocated in a fixed volume of receptor solution. The entire receptor solution is changed at each sampling time. The temperature of the receptor solution in the water bath is maintained at 35° C.

Example 6

The warfarin/permeation enhancer reservoirs are prepared by mixing warfarin, EtOH, GML, and caproyl lactic acid (CLA) (R.I.T.A. Corp., Woodstock, Ill.).

An additional 3% by weight hydroxypropylcellulose and water are added and the mixture is placed in a suitable container and gelled. A desired quantity of the mixture is applied on the surface of a previously formed trilaminate consisting of a 0.5 mm thick ethylene vinyl acetate film having a vinyl acetate content of 18% for use as a rate controlling membrane; a polyisobutylene contact adhesive containing 2.5% by weight warfarin; and a polyethylene ethylene terephthalate film coated with silicone for use as a release liner. A Medpar backing is applied on top of the mixture and the entire system is heat sealed. The systems are die-cut to the required sizes for use in the in vitro test method described in Examples 4 and 5.

Example 7

A desired quantity of the mixture as formed in Example 6 is applied on the surface of a previously formed trilaminate consisting of a 0.5 mm thick ethylene vinyl acetate film having a vinyl acetate content of 28% for use as a rate controlling membrane; a polyisobutylene contact adhesive containing 2.5% by weight warfarin; and a polyethylene ethylene terephthalate film coated with fluorocarbon for use as a release liner. A Medpar backing is then applied on top of the mixture and the entire system is heat sealed. The systems are then die-cut to the required sizes for use in the in vitro test method described in Examples 2-4.

Example 8

The effect of mineral oil on the permeation enhancement of GML with various cosolvents is studied. The warfarin/permeation enhancer reservoirs are prepared by mixing ethylene vinyl acetate having a vinyl acetate content of 40 percent ("EVA 40", USI Chemicals, Illinois), warfarin mesylate, GML, and a cosolvent selected from Laureth-4 (L-4) (Heterene Chemical Co., Inc., Paterson, N.J.), methyl laurate (Sigma), lauryl lactate (ISP Van Dyk Inc., Belleville, N.J.) and dodecyl acetate (Penta). The mixture is dissolved in tetrahydrofuran. After blending, the mixture is hand cast and dried to a 0.12 mm. thick film. Various compositions for each cosolvent without mineral oil are compared with a control composition comprising mesylate/GML/laureth-4/EVA 10/20/12/58.

The film is laminated to a PET/EVA (3M Corp., St. Paul, Minn.) backing on one side. The systems are die-cut to the required sizes for use in the in vitro test method described in Examples 5-7.

Example 9

Several test samples are made to measure the flux of warfarin through human cadaver epidermis from donor vehicles containing the warfarin mixed with water alone, water and ethanol, or mineral oil alone. Transdermal fluxes are obtained using human epidermis at 35° C. in standard diffusion cells.

Having thus generally described our invention and described certain specific embodiments thereof, including the embodiments that applicants consider the best mode of practicing their invention, it should be readily apparent that various modifications to the invention may be made by workers skilled in the art without departing from the scope of this invention which is limited only by the following claims.

What is claimed is:

1. A delivery system for transdermal administration of warfarin to a patient, comprising:
a delivery device having a backing layer, a hydrophobic reservoir disposed on said backing layer, said reservoir having a skin-facing surface and an amount of base form warfarin disposed in a hydrophobic polymeric carrier in said hydrophobic reservoir, said hydrophobic polymeric carrier being selected from the group consisting of polyurethane, ethylene/vinyl acetate copolymer (EVA), and styrenic block copolymer.

2. The system of claim 1, wherein said amount of warfarin in said hydrophobic reservoir is no greater than a saturation concentration of said warfarin, whereby said hydrophobic reservoir is substantially free of warfarin crystals.

3. The system of claim 1, wherein said hydrophobic reservoir includes in the range of approximately 1-30 wt. % warfarin.

4. The system of claim 1, where said hydrophobic reservoir includes in the range of approximately 7-21 wt. % warfarin.

5. The system of claim 1, wherein said warfarin solubility in said hydrophobic reservoir is in the range of approximately 0.1-22 wt. %.

6. The system of claim 1, wherein said warfarin solubility in said hydrophobic reservoir is in the range of approximately 2.0-15 wt. %.

7. The system of claim 1, wherein said hydrophobic reservoir includes a first permeation enhancer.

8. The system of claim 7, wherein said first permeation enhancer is selected from the group consisting of glycerin fatty acid esters, isosorbide fatty acid esters, sucrose, polyethylene glycol; caproyl lactylic acid; laureth-2; laureth-2 acetate; laureth-2 benzoate; laureth-3 carboxylic acid; laureth-4; laureth-5 carboxylic acid; oleth-2; glyceryl pyroglutamate oleate; glyceryl oleate; N-lauroyl sarcosine; N-myristoyl sarcosine; N-octyl-2-pyrrolidone; lauraminopropionic acid; polypropylene glycol-4-laureth-2; polypropylene glycol-4-laureth-5dimethyl lauramide; lauramide diethanolamine (DEA), monoglycerides such as glycerol monolaurate (GML), glycerol monooleate (GMO) or glycerol monolinoleate, glyceryl monocaprylate, glyceryl monocaprate, lactate esters such as lauryl lactate, methyl laurate, caproyl lactic acid, lauramide diethanolamine (LDEA), dimethyl lauramide, polyethylene glycol-4 lauryl ether (Laureth-4), lauryl pyroglutamate (LP), sorbitan monolaurate and ethanol.

9. The system of claim 1, wherein said skin-facing surface of said hydrophobic reservoir is substantially adhesive.

10. The system of claim 1, wherein said hydrophobic reservoir is formed from an adhesive member.

11. The system of claim 1, wherein said device includes an adhesive layer disposed on said skin-facing surface of said hydrophobic reservoir.

12. The system of claim 1, wherein said device includes a first rate-controlling membrane disposed on said skin-facing surface of said hydrophobic reservoir, said first rate-controlling membrane having a skin-facing surface.

13. The system of claim 12, wherein said skin-facing surface of said first rate controlling membrane is substantially adhesive.

14. The system of claim 7, wherein said device includes a permeation enhancer reservoir, said permeation reservoir having a second permeation enhancer disposed therein.

15. The system of claim 14, wherein said second permeation enhancer is selected from the group consisting of glycerin fatty acid esters, isosorbide fatty acid esters, sucrose, polyethylene glycol; caproyl lactylic acid; laureth-2; laureth-2 acetate; laureth-2 benzoate; laureth-3 carboxylic acid; laureth-4; laureth-5 carboxylic acid; oleth-2; glyceryl pyroglutamate oleate; glyceryl oleate; N-lauroyl sarcosine; N-myristoyl sarcosine; N-octyl-2-pyrrolidone; lauraminopropionic acid; polypropylene glycol-4-laureth-2; polypropylene glycol-4-laureth-5dimethyl lauramide; lauramide diethanolamine (DEA), monoglycerides such as glycerol monolaurate (GML), glycerol monooleate (GMO) or glycerol monolinoleate, glyceryl monocaprylate, glyceryl monocaprate, lactate esters such as lauryl lactate, methyl laurate, caproyl lactic acid, lauramide diethanolamine (LDEA), dimethyl lauramide, polyethylene glycol-4 lauryl ether (Laureth-4), lauryl pyroglutamate (LP), sorbitan monolaurate and ethanol.

16. The system of claim 15, wherein said permeation enhancer reservoir includes in the range of approximately 5-25 wt. % of said permeation enhancer.

17. The system of claim 15, wherein said permeation enhancer reservoir includes in the range of approximately 10-20 wt. % of said permeation enhancer.

18. The system of claim 14, wherein said device includes an enhancer rate-controlling membrane disposed between said permeation enhancer reservoir and said hydrophobic reservoir.

19. The system of claim 1, wherein said hydrophobic reservoir is formed from a material selected from the group consisting of polyurethane, polysiloxanes, polyisobutylene (Pifi), polyisoprene, polybutadiene, ethylene/vinyl acetate copolymer (EVA), polyacrylate, styrenic block copolymers, styrene-isoprene-styrene block copolymer (SIS), styrene-butadiene-styrene copolymer (SBS), styrene-ethylenebutene-styrene copolymers (SEBS), and di-block analogs thereof.

20. A method for transdermal administration of warfarin to a patient, comprising the steps of:
providing a delivery device, said delivery device including a hydrophobic reservoir having base form warfarin disposed in a hydrophobic carrier polymer, said hydrophobic polymeric carrier being selected from the group consisting of polyurethane, ethylene/vinyl acetate copolymer (EVA), and styrenic block copolymer; and
applying said delivery device to the skin of the patient for an administration period of at least 8 hrs wherein said warfarin is systemically delivered to the patient at a therapeutically effective rate.

21. The method of claim 20, wherein said hydrophobic reservoir includes in the range of approximately 1-30 wt. % warfarin.

22. The method of claim 20, wherein said hydrophobic reservoir includes in the range of approximately 7-21 wt. % warfarin.

23. The method of claim 20, wherein said administration period is in the range of approximately 3-7 days.

24. The method of claim 20, wherein said administration period is in the range of approximately 3-4 days.

25. The method of claim 20, wherein said warfarin delivery produces a warfarin blood plasma level in the range of approximately 0.1-4 ng/mL-cm$^2$.

26. The method of claim 20, wherein said warfarin delivery produces a warfarin blood plasma level in the range of approximately 1.0-2.0 ng/mL-cm$^2$.

27. The method of claim 24, wherein said warfarin delivery provides a substantially constant warfarin blood plasma level over said administration period.

28. The method of claim 24, wherein at least 3% and less than 40% of said warfarin disposed in said hydrophobic reservoir is delivered to the patient in the first 24 hrs. of said administration period.

29. The method of claim 24, wherein at least 6% and less than 50% of said warfarin disposed in said hydrophobic reservoir is delivered to the patient in the first 48 hrs. of said administration period.

30. The method of claim 24, wherein at least 10% and less than 75% of said warfarin disposed in said hydrophobic reservoir is delivered to the patient over said administration period.

31. The method of claim 20, wherein said warfarin delivery produces an International Normalized Ratio in the range of approximately 1.25- 2.

32. The method of claim 20, wherein at least 0.5-2 mg of warfarin is delivered to the patient over 24 hrs.

33. The method of claim 20, including the step of administering a permeation enhancer, said permeation enhancer being disposed in said hydrophobic reservoir.

34. The method of claim 33, wherein said permeation enhancer is selected from the group consisting of glycerin fatty acid esters, isosorbide fatty acid esters, sucrose, polyethylene glycol; caproyl lactylic acid; laureth-2; laureth-2 acetate; laureth-2 benzoate; laureth-3 carboxylic acid; laureth-4; laureth-5 carboxylic acid; oleth-2; glyceryl pyroglutamate oleate; glyceryl oleate; N-lauroyl sarcosine; N-myristoyl sarcosine; N-octyl-2-pyrrolidone; lauraminopropionic acid; polypropylene glycol-4-laureth-2; polypropylene glycol-4-laureth-5 dimethyl lauramide; lauramide diethanolamine (DEA), monoglycerides such as glycerol monolaurate (GML), glycerol monooleate (GMO) or glycerol monolinoleate, glyceryl monocaprylate, glyceryl monocaprate, lactate esters such as lauryl lactate, methyl laurate, caproyl lactic acid, lauramide diethanolamine (LDEA), dimethyl lauramide, polyethylene glycol-4 lauryl ether (Laureth-4), lauryl pyroglutamate (LP), sorbitan monolaurate and ethanol.

35. A delivery system for transdermal administration of warfarin to a patient, comprising:
a delivery device having a backing layer, a hydrophobic reservoir disposed on said backing layer, said reservoir having an amount of base form warfarin disposed in a hydrophobic polymeric carrier in said hydrophobic reservoir, and an in-line skin contacting adhesive disposed in the device for contacting the skin.

36. A delivery system for transdermal administration of warfarin to a patient, comprising:
a delivery device having a backing layer, a hydrophobic reservoir disposed on said backing layer, said reservoir having an amount of base form warfarin disposed in a hydrophobic polymeric carrier in said hydrophobic reservoir, and an in-line skin contacting adhesive disposed in the device for contacting the skin, and a rate control membrane disposed between the hydrophobic reservoir and the in-line skin contacting adhesive.

* * * * *